US012577204B2

(12) United States Patent
Haydl et al.

(10) Patent No.: US 12,577,204 B2
(45) Date of Patent: Mar. 17, 2026

(54) SOLUTION OF TEMPO-DERIVATIVES FOR USE AS ELECTROLYTE IN REDOX-FLOW CELLS

(71) Applicant: BASF SE, Ludwigshafen am Rhein (DE)

(72) Inventors: Alexander Michael Haydl, Ludwigshafen am Rhein (DE); Peter Oechsle, Ludwigshafen am Rhein (DE); Harald Winsel, Ludwigshafen am Rhein (DE); Jan-Dirk Arndt, Ludwigshafen am Rhein (DE); Joaquim Henrique Teles, Ludwigshafen am Rhein (DE); Johann-Peter Melder, Ludwigshafen am Rhein (DE); Olaf Kriha, Ludwigshafen am Rhein (DE); Rainer Klopsch, Ludwigshafen am Rhein (DE)

(73) Assignee: BASF SE, Ludwigshafen Am Rhein (DE)

( * ) Notice: Subject to any disclaimer, the term of this patent is extended or adjusted under 35 U.S.C. 154(b) by 567 days.

(21) Appl. No.: 17/915,117

(22) PCT Filed: Mar. 22, 2021

(86) PCT No.: PCT/EP2021/057180

§ 371 (c)(1),
(2) Date: Sep. 28, 2022

(87) PCT Pub. No.: WO2021/197876

PCT Pub. Date: Oct. 7, 2021

(65) Prior Publication Data

US 2023/0150939 A1 May 18, 2023

(30) Foreign Application Priority Data

Apr. 1, 2020 (EP) .................................... 20167462

(51) Int. Cl.
*C07D 211/58* (2006.01)
*H01M 8/18* (2006.01)

(52) U.S. Cl.
CPC ........... *C07D 211/58* (2013.01); *H01M 8/188* (2013.01)

(58) Field of Classification Search
CPC ............................ C07D 211/58; H01M 8/188
See application file for complete search history.

(56) References Cited

U.S. PATENT DOCUMENTS

2018/0241065 A1* 8/2018 Schubert ............... H01M 8/188

FOREIGN PATENT DOCUMENTS

| | | | |
|---|---|---|---|
| DE | 102015010083 | A1 | 2/2017 |
| DE | 102016009904 | A1 | 2/2018 |
| WO | 2014/026728 | A1 | 2/2014 |
| WO | 2018/028830 | A1 | 2/2018 |

OTHER PUBLICATIONS

European Search Report for EP Patent Application No. 20167462.9, Issued on Oct. 14, 2020, 4 pages.
Hu et al., "Improved radical stability of viologen anolytes in aqueous organic redox flow batteries," Chemical Communications, vol. 54, No. 50, Jun. 19, 2018, pp. 6871-6874.
International Preliminary Report on Patentability received for PCT Patent Application No. PCT/EP2021/057180, mailed on Oct. 13, 2022, 8 pages.
Janoschka et al., "An Aqueous Redox-Flow Battery with High Capacity and Power: The TEMPTMA/MV System," Angewandte Chemie, vol. 55, Issue 46, Nov. 7, 2016, pp. 14427-14430.
International Search Report and Written Opinion received for PCT Patent Application No. PCT/EP2021/057180, mailed on Jun. 30, 2021, 12 pages.

* cited by examiner

*Primary Examiner* — Timothy R Rozof
(74) *Attorney, Agent, or Firm* — Faegre Drinker Biddle & Reath LLP

(57) ABSTRACT

The present invention relates to a solution comprising water and different 2,2,6,6-tetramethyl-piperidinyl-oxyl (TEMPO)-derivatives, a process for the production of this solution, a process for making a redox-flow cell comprising the solution as electrolyte, a redox-flow cell comprising the solution as an electrolyte in one chamber of the cell and the use of the redox-flow cell for storing electrical energy.

18 Claims, 3 Drawing Sheets

SOLUTION OF TEMPO-DERIVATIVES FOR USE AS ELECTROLYTE IN REDOX-FLOW CELLS

CROSS-REFERENCE TO RELATED APPLICATIONS

This application is a national stage application (under 35 U.S.C. § 371) of PCT/EP2021/057180, filed Mar. 22, 2021, which claims benefit of European Application No. 20167462.9, filed Apr. 1, 2020, both of which are incorporated herein by reference in their entirety.

The present invention relates to a solution comprising water and different 2,2,6,6-Tetramethylpiperidinyl-oxyl (TEMPO)-derivates, a process for the production of this solution, a process for making a redox-flow cell comprising the solution as electrolyte, a redox-flow cell comprising the solution as an electrolyte in one chamber of the cell and the use of the redox-flow cell for storing electrical energy.

There is a huge demand for storing electrical energy for different kind of applications. It was found that redox-flow cells with new organic compounds as redox couple comprising 2,2,6,6-tetramethylpiperidinyl-oxyl (TEMPO)-derivates with redox active potential separated from each other by using a membrane which selects the molecules by size might be an easy and inexpensive way to provide a long-living redox-flow cell which will not have a negative impact on the environment as it is described in WO 2014/26728.

WO2018/028830 describes a process of the production of 4-ammonium-2,2,6,6-tetraalkylpiperidinyl salts as typical TEMPO-derivates which are such redox active compounds that are normally used in the cathode chamber of a redox-flow cell. It is disclosed that for the production of these compounds 3 different production ways are possible. Starting products are always solutions of either 4-oxo-alkylpiperidine, the corresponding imine or 4-amino-alkylpiperdine dissolved in different kinds of organic aprotic solvents like alcohols, ethers, nitriles, halogenated hydrocarbons, aromatic hydrocarbons, aliphatic hydrocarbons or mixtures of them. In two production process described in WO 2018/028830 the intermediate compounds are solids which have to be separated from the solvent by filtration or centrifugation before using them into the next step. Additionally, the oxidation step described in WO 2018/028830 requires the addition of base to keep the pH-value during oxidation in the optimum range. With these described production processes, a very pure compound is obtained but there are a lot of intermediate stages where solids have to be separated and handled, reaction steps where complex handling of the solutions is necessary. The state-of-the-art process uses several different solvents or mixtures of solvents, making solvent recycling particularly complicated. In one of the processes an anion exchange is required because bromide cannot be tolerated in the electrolyte solution since it is easily oxidizable. Furthermore, a production process where mainly water is used as solvent and where the anion can be chosen at will without the need of using ion-exchanging is not described. For an industrial scale production, the described production processes are not appropriate as every filtration step, solid handling step, solvent change or anion exchange step causes great losses in yields and time and increases the complexity of the process. Furthermore, the addition of extra base during the oxidation step causes additional cost and effort if additional salts are to be removed from the electrolyte solution.

DE 102015010083 A1 and B. Ho in Angewandte Chemie vol. 55, no. 46 of Oct. 18, 2016 on page 14427-14430 disclose a method for synthesizing compound of formula (I), as well as the use of compound of formula (I) as catholyte material in a redox-flow cells. Both disclosures do not describe the production of an aqueous solution comprising compounds of formula (II) and (III) beside compound of formula (I) and the preferred use of such an aqueous solution as a catholyte in a redox-flow cell.

T. Janoschka et al. describe in Chemical Communications vol 54, no. 50 of Jun. 19, 2018 on page 6871-6874 an aqueous organic redox-flow battery comprising compound of formula (I) but not the use of an aqueous solution comprising compounds of formula (II) and (III) beside compound of formula (I) as catholyte in a redox-flow cell of a redox-flow battery.

Therefore, it is an object of the present invention to provide an aqueous solution comprising different TEMPO-derivates with chemical redox potential comparable to those of the pure TEMPO-derivates described in the state of the art by using an easy and inexpensive way of production of this solution, where the anions in the resulting solution can be chosen at will, no base addition is required during oxidation and which can be used on industrial scale without high efforts and great losses of yield. Another object of the present invention is to provide a redox-flow cell comprising an aqueous solution of TEMPO-derivates that shows similar or equal properties for storing energy than the state of the art redox-flow cell comprising an aqueous solution of 2,2,6,6-tetramethyl-1-piperidinyloxy-4-trimethylammoniumchloride.

The problem will be solved by a solution comprising a) water, b) 20 to 55 wt.-% according to the total weight amount of the solution of compound 2,2,6,6-tetramethyl-4-(trimethylammonio)-1-piperidinyloxy of formula (I), (I)

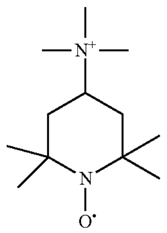

c) less than 0.1 wt.-% according to the total weight amount of the solution alkali metal cation d) 0.1 to 12.5 wt.-% according to the total weight amount of the solution of compound N,N,N,1,2,2,6,6-octamethyl-4-piperidinammonium-1-oxide of formula (II)

(II)

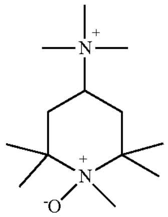

e) 0.01 to 20 wt.-% according to the total weight amount of the solution of compound 2,2,6,6-hexamethyl-4-(dimethylamino)-1-piperidinyloxy-N-oxide of formula (III)

(III)

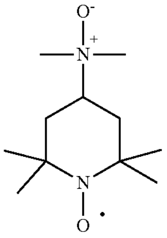

The inventive solution will be advantageous if the alkali metal cation is Na.

The inventive solution will be advantageous if the pH-value is in the range of 2 to 7.

The inventive solution will be advantageous if the sum of the amounts of the compounds of formula (I), (II), (III) plus the amounts of alkali metal cations in the solution is in the range of 20 to 50 wt.-% with respect to the total weight amount of the solution.

A further embodiment of the invention is a process for the production of the inventive solution comprising the following steps:

i) reacting the compound N,N,2,2,6,6-hexamethyl-4-piperidinamine of formula (IV)

(IV)

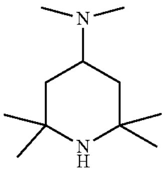

with dimethyl carbonate in the presence of a saturated $C_1$ to $C_4$ alcohol to obtain a mixture comprising compound N,N,N,2,2,6,6-heptamethyl-4-piperidinaminium of formula (V), compound N,N,N,1,2,2,6,6-octamethyl-4-piperidinaminium of formula (VI) and non-reacted compound N,N,2,2,6,6-hexamethyl-4-piperidinamine of formula (IV) dissolved in the saturated $C_1$ to $C_4$ alcohol (IV)

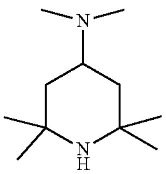

(V)

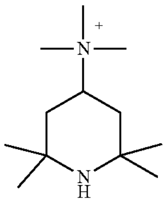

-continued (VI)

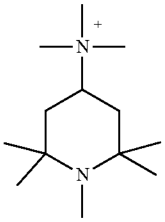

ii) making a solvent change from the $C_1$ to $C_4$ alcohol to water iii) reacting the resulting aqueous mixture of step ii) with an aqueous hydrogen peroxide solution, iv) adding an acid to the resulting mixture of step iii) until the pH-value decreases to the range of 3 to 5, v) partially removing the water of the resulting mixture of step iv) until the concentration of compound of formula (I) is in the range of 20 to 55 wt.-% according to the inventive solution.

The inventive process will be advantageous if in step i) of the inventive process the compound of formula (IV) is reacted with dimethyl carbonate in the presence of a saturated $C_1$ to $C_4$ alcohol at a temperature in the range of 90 to 170° C.

The inventive process will be advantageous if in step i) of the inventive process the compound of formula (IV) is reacted with 0.7 to 1.5 mol dimethyl carbonate per mol of compound of formula (IV) in the presence of a saturated $C_1$ to $C_4$ alcohol and the mass ratio between compound of formula (IV) in the feed mixture and the saturated $C_1$ to $C_4$ alcohol is in the range of 0.1 to 5.

The inventive process will be advantageous if in step iii) of the inventive process the resulting mixture of step ii) is reacted with an aqueous hydrogen peroxide solution at a temperature in the range of 20 to 80° C.

The inventive process will be advantageous if in step iii) of the inventive process 1.5 to 5 mol of aqueous hydrogen peroxide having a concentration in the range of 25 to 70 wt.-% are used per mol of compound of formula (IV) in the feed mixture.

The inventive process will be advantageous if the addition of the acid in step iv) starts when the concentration of hydrogen peroxide in the mixture of step iii) has decreased to less than 0.5 wt.-%.

The inventive process will be advantageous if the acid used in step iv) has a standard redox potential greater than +1.35 V.

The inventive process will be advantageous if in step ii) of the inventive process the $C_1$ to $C_4$ alcohol is first distilled off and the remaining material is dissolved in water.

The inventive process will be advantageous if in step ii) of the inventive process water is added to the resulting mixture of step i) and afterwards or simultaneously the $C_1$ to $C_4$ alcohol is distilled off.

The inventive process will be advantageous if the saturated $C_1$ to $C_4$ alcohol is selected from the group of methanol and n-butanol.

A further embodiment is a process for making a redox-flow cell wherein the inventive solution is used as electrolyte in one of both chambers of the cell.

The inventive process for making a redox-flow cell will be advantageous if the process comprises the following steps:

a) providing two chambers for catholyte and anolyte solutions, each connected to at least one storage tank for catholyte and anolyte solutions respectively
b) separating the two chambers with an ion-conducting membrane
c) equipping the chambers with electrodes
d) filling the inventive solution as redox active material in the catholyte chamber
e) filling an anolyte solution comprising another redox active material in the anolyte chamber.

A further embodiment of the invention is the redox-flow cell obtained by the inventive process for making a redox-flow cell.

A further embodiment of the invention is the use of the inventive redox flow cell for storing electrical energy.

The inventive solution comprising water, 20 to 55 wt.-% according to the total weight amount of the solution of compound 2,2,6,6-tetramethyl-4-(trimethylammonio)-1-piperidinyloxy of formula (I), less than 0.1 wt.-% according to the total weight amount of the solution alkali metal cation, 0.1 to 12.5 wt.-% according to the total weight amount of the solution of compound N,N,N,1,2,2,6,6-octamethyl-4-piperidinammonium-1-oxide of formula (II) and 0.01 to 20 wt.-% according to the total weight amount of the solution of compound 2,2,6,6-hexamethyl-4-(dimethylamino)-1-piperidinyloxy-N-oxide of formula (III).

The compound of formula (I) is preferably the main compound according to all compounds of formula (I), (II), (III) and the alkali metal cation in the inventive solution. Preferably, the amount of compound of formula (I) in the inventive solution is in the range of 25 to 50 wt.-%, particular in the range from 35 to 50 wt.-%, more preferably in the range of 40 to 45 wt.-% according to the total amount of the solution.

The inventive solution also comprises alkali metal cations. Preferably, these alkali metal cations are selected from the group of Na and K, more preferably is Na as alkali metal cation. The amount of the alkali metal cation in the inventive solution is preferably less than 0.1 wt.-%, particular in the range from 0.001 to 0.01 wt.-%, more preferably in the range of 0.001 to 0.008 wt.-% according to the total amount of the solution.

The compound of formula (II) is one resulting from the oxidation of one of the two byproducts formed by methylation of the starting compound of formula (IV) in the inventive process. Preferably, the amount of compound of formula (II) in the inventive solution is in the range from 0.1 to 12.5 wt.-%, particularly in the range of 0.1 to 5.0 wt.-%, more preferably in the range of 0.3 to 2.0 wt.-% according to the total amount of the solution.

The compound of formula (III) is the other or second resulting from the oxidation of one of the two byproducts formed by methylation of the starting compound of formula (IV) in the inventive process. Preferably, the amount of compound of formula (III) in the inventive solution is in the range of 0.01 to 20 wt.-%, particularly in the range from 0.01 to 5.0 wt.-%, more preferably in the range of 0.02 to 1.0 wt.-% according to the total amount of the solution.

The sum of all amounts of compounds of formula (I), (II), (III) and the alkali metal cation is preferably in range from 20 to 50 wt.-%, particular in the range from 30 to 50 wt.-%, more preferably in the range from 40 to 50 wt.-% according to the total amount of the solution.

The amount of water in the inventive solution is preferably in the range from 35 to 75 wt.-% particularly in the range from 45 to 70 wt.-%, more preferably in the range from 50 to 60 wt.-% according to the total amount of the solution.

Preferably the pH-value of the inventive solution is in the range of 2 to 7, particularly in the range of 3 to 5, more preferably in the range of 4 to 5.

In the inventive solution, the anions present as counterions for the cationic species, are selected from the group of chloride, fluoride, perchlorate, sulfate, alkylsulfonate, arylsulfonate, phosphate, alkylphosphonate, arylphosphonate and nitrate or mixtures thereof. Preferably the anions are selected from the group of chloride, nitrate, sulfate and perchlorate, more preferably the anion is chloride.

The inventive solution is obtained by the inventive process. The inventive process comprises the following steps:

i) reacting the compound N,N,2,2,6,6-hexamethyl-4-piperidinamine of formula (IV)

(IV)

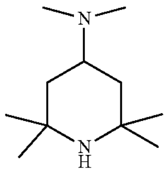

with dimethyl carbonate in the presence of a saturated $C_1$ to $C_4$-alcohol to obtain a mixture comprising compound N,N,N,2,2,6,6-heptamethyl-4-piperidinaminium of formula (V), compound N,N,N,1,2,2,6,6-octamethyl-4-piperidinaminium of formula (VI) and non-reacted compound N,N,2,2,6,6-hexamethyl-4-piperidinamine of formula (IV) dissolved in the saturated $C_1$ to $C_4$ alcohol (IV)

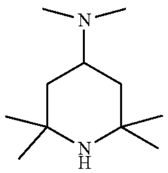

(V)

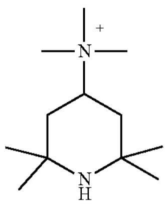

(VI)

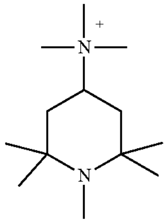

ii) making a solvent change from the $C_1$ to $C_4$ alcohol to water
iii) reacting the resulting aqueous mixture of step ii) with an aqueous hydrogen peroxide solution, iv) adding an acid to the resulting mixture of step iii) until the pH-value is in the range of 2 to 7, v) partially removing the water of the resulting mixture of step iv) until the concentration of compound of formula (I) is in the range of 20 to 55 wt.-% according to the inventive solution.

For the first step i) the compound of formula (IV) is dissolved in a saturated $C_1$ to $C_4$ alcohol. A saturated $C_1$ to $C_4$ alcohol means an alcohol selected from the group of methanol, ethanol, n-propanol, iso-propanol, n-butanol, 2-butanol, iso-butanol and tert-butanol. The use of methanol and n-butanol is preferred, more preferably is the use of methanol. Preferably, the mass ratio between the compound of formula (IV) in the feed mixture and the used saturated $C_1$ to $C_4$ alcohol in the first step i) of the inventive process is in the range from 0.1 to 5, particular in the range from 0.3 to 2, more preferably in the range from 0.7 to 1.2. The phrase "of compound of formula (IV) in the feed mixture" shall mean the amount of compound of formula (IV) that is dissolved in the saturated $C_1$ to $C_4$ alcohol in step i) at the beginning and not the amount of compound of formula (IV) that still remains in the solution after methylation in step i).

In the first step i) of the inventive process the compound of formula (IV) dissolved in a saturated $C_1$ to $C_4$ alcohol and is methylated with dimethyl carbonate. Preferably, the alcoholic solution of compound of formula (IV) is methylated with 0.7 to 1.5 mol, particularly 0.9 to 1.5 mol, more preferably with 1.0 to 1.2 mol dimethyl carbonate per mol of compound of formula (IV) in the feed mixture used. During this methylation the temperature of the reaction is preferably in the range of 90 to 170° C., particularly in the range from 100 to 160° C., more preferably between 120 to 140° C.

After the methylation in step i) of the inventive process is completed a solvent change from the $C_1$ to $C_4$ alcohol to water as solvent will be performed as in step ii) of the inventive process. The solvent change can be conducted in two different ways. One way is to distill the $C_1$ to $C_4$ alcohol completely off so that a resulting solid material comprising the methylated compounds of formula (V), (VI) and the unreacted compound of formula (IV) is obtained. The resulting solid material will be dissolved in water afterwards.

The other, and more preferred way of solvent change is to add water to the resulting alcoholic solutions of step i) of the inventive process first, and subsequently removing the $C_1$ to $C_4$ alcohol either as light boiler or in form of the light boiling azeotrope with water. In a more preferred way, the addition of water and the remove of die $C_1$ to $C_4$ alcohol can happen simultaneously. This process step where water is added first or simultaneously while the $C_1$ to $C_4$ alcohol is removed, is preferred as no solid material has to be handled. Furthermore, if methanol or n-butanol as preferred $C_1$ to $C_4$ alcohol in step i) of the inventive process is used, they can easily be removed after the addition of water in step ii) of the inventive process. The methanol can be distilled off as light boiler while n-butanol is distilled off as the heteroazeotrope with water. If butanol is used resulting aqueous phase obtained after condensation and phase separation can be returned into step i) of the inventive process. Both alcohols-methanol and n-butanol—can be recycled into step i) of the inventive process without any further cleaning or drying steps. If ethanol, n-propanol, iso-propanol, iso-butanol or tert-butanol are used in step i) of the inventive process then these alcohols will be removed via distillation. These removed alcohols must be dried before recycling them to step i) of the inventive process. The use of methanol as the solvent is particularly advantageous because it does not form an azeotrope with water and can be removed as the light boiler, making a separate drying step unnecessary. The recovered methanol can thus be used in step i) without further processing.

The resulting aqueous solution of step ii) of the inventive process comprises water, the compounds of formula (V), (VI) and unreacted compound of formula (IV) and carbonate or methylcarbonate as counterions. This resulting aqueous mixture of step ii) reacts with an aqueous hydrogen peroxide solution in step iii) of the inventive process.

Step iii) of the inventive process is an oxidation step wherein the compounds of formula (IV), (V) and (VI) are oxidized to the compounds of formula (I), (II) and (III). Therefore, the resulting aqueous mixture of step ii) reacts with 1.5 to 5 mol, particular with 1.5 to 3 mol, more preferably with 1.7 to 2.3 mol of hydrogen peroxide per mol of the compound of formula (IV) in the feed mixture used in step i) of the inventive process, whereas the hydrogen peroxide is used as an aqueous solution.

Preferably the concentration of the used aqueous hydrogen peroxide solution in step iii) of the inventive process is in the range from 25 to 70 wt.-%, particularly 30 to 70 wt.-%, more preferably 45 to 70 wt.-% of hydrogen peroxide.

During the oxidation the temperature of step iii) of the inventive process is preferably in the range from 20 to 80° C., particularly in the range from 40 to 60° C., more preferably in the range from 50 to 60° C.

After finishing the addition of the aqueous hydrogen peroxide solution, the resulting mixture of step iii) of the inventive process will be stirred at the condition of step iii), which means around 60° C., until the concentration of hydrogen peroxide in this solution is less than 0.5 wt.-%. The amount of hydrogen peroxide remaining is determined by cerimetric titration of the solution before and after catalytic decomposition of hydrogen peroxide with manganese dioxide. The difference between the two titration values is used to calculate the residual amount of hydrogen peroxide.

After the addition of the aqueous hydrogen peroxide solution is completed and the hydrogen peroxide concentration has decreased to less than 0.5 wt.-% step iii) is finished. In step iv) an acid is added to the solution obtained in step iii) to adjust the pH-value. Preferably the pH-value is adjusted in the range from 2 to 7, particularly in the range from 3 to 5, more preferably in the range from 4 to 5 by the addition of acid. The acid used for adjusting the pH-value is one that-30 has a standard redox potential greater than +1.35 V. Preferably, the acid is selected from the group of hydrogen chloride, perchloric acid, sulfuric acid, phosphoric acid, nitric acid and methanesulfonic acid, particularly the acids are hydrogen chloride and perchloric acid, more preferably is hydrogen chloride. Hydrogen chloride can be added as a gas or in form of an aqueous solution. Preferably an aqueous solution of hydrogen chloride, commonly known as hydrochloric acid is used.

In the last step of the inventive process the amount of water is reduced in step v) of the inventive process. This will be done by distillation. The amount of water that is distilled off depends on the desired final concentration of compound of formula (I) in the final solution. Water must be distilled off until the resulting solution shows a content of compound of formula (I) in the range of 20 to 55 wt.-%, preferably in the range from 25 to 50 wt.-%, particular in the range from 35 to 50 wt.-%, more preferably in the range from 40 to 45 wt.-% according to the total weight amount of the solution. Preferably the distillation will be done at a pressure in the range of 0.02 to 1.0 bar and a temperature in the range of 20 to 100° C., particular at a pressure in the range of 0.05 to 0.3 bar and a temperature in the range of 30 to 70° C., more preferably at a pressure in the range of 0.08 to 0.2 bar and a temperature in the range of 58 to 62° C.

After concentration, the inventive solution obtained can be used without further treatment as an electrolyte in a redox-flow cell. Preferably the inventive solution is used as catholyte in such a redox-flow cell. The redox-flow cell is normally built up by using two chambers for catholyte and anolyte solution each connected via a pump to a storage tank for catholyte and anolyte solution respectively. Both chambers are separated by an ion-conducting membrane and equipped with electrodes. In the cathode chamber and the connected storage tank of the cathode the inventive solution is filled. In the anode chamber and the connected storage tank of the anode the electrolyte for the anode is filled. The redox active compounds in the redox-flow cell change during charging and discharging between their different redox levels. For discharging the electrolyte has to be pumped from the storage tank to the electrode while for charging the inverse process is used. Therefore, the redox-flow cell comprising the inventive solution as electrolyte is an easy and multifunctional way to storage electrical energy for different applications.

EXAMPLES

General pH-Values:

pH values are always measured using a calibrated glass electrode (EasyFerm Plus PHI S8 225, two-point calibration with buffer pH=4.00 (citric acid, sodium hydroxide, sodium chloride from Fluka) and buffer pH=7.00 (potassium dihydrogen phosphate, disodium hydrogen phosphate from Fluka).

$^1$H-NMR Method:

1H-NMR Data of Compound of Formula (V):

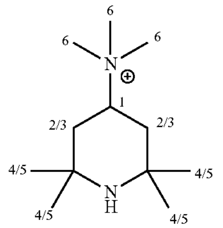

$^1$H-NMR (500 MHz, $D_2O$): δ [ppm]=3.68 (tt, J=12.5 Hz, 2.8 Hz 1H, $H_1$), 3.07 (s, 9H, $H_6$), 2.02-2.08 (m, 2H, $H_3$), 1.32 (t, J=12.5 Hz, 2H, $H_2$), 1.14 (s, 6H, $H_5$), 1.12 (s, 6H, $H_4$).

5. $^1$H-NMR Data of Compound of Formula (VI):

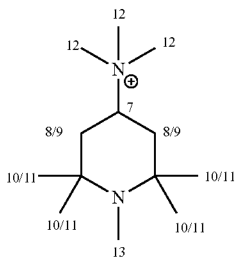

$^1$H-NMR (500 MHz, $D_2O$): δ [ppm]=3.62 (tt, J=12.5 Hz, 3.1 Hz, 1H, $H_7$), 3.00 (8, 9H, $H_{12}$), 2.15 (s, 3H, $H_{13}$), 2.08-2.02 (m, 2H, $H_9$), 1.55 (t. J=12.5 Hz, 2H, $H_8$), 1.15 (s, 6H, $H_{11}$), 1.05 (s, 6H, $H_{10}$).

$^1$H-NMR Data of Compound of Formula (V):

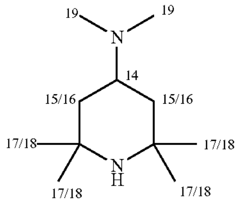

$^1$H-NMR (500 MHz, $D_2O$): δ [ppm]=2.83 (tt, J=12.3 Hz, 3.2 Hz, 1H, $H_{14}$), 2.27 (s, 6H, $H_{19}$), 1.88 (dd, J=12.7 Hz, 3.2 Hz, 2H, $H_{15}$), 1.28 (s, 6H, $H_{17}$), 1.24 (s, 6H, $H_{18}$), 1.17 (dd, J=12.7 Hz, 12.3 Hz, 6H, $H_{16}$).

The molar ratio of compound of formula (IV), (V) and (VI) can be determined most conveniently by comparing the integrals of the $^1$H-NMR signals at δ=3.68 ppm (1H from compound of formula (V)), 2.15 ppm (3H from compound of formula (VI) and 2.27 ppm (6H from compound of formula (IV)).

Thus the molar ratio of compound of formula (IV):(V):(VI) is the same as the ratio of the following integrals:

(integral of signal at δ=3.68 ppm from compound of formula (V)):(integral of signal at δ=2.15 ppm from compound of formula (IV))/3:(integral of signal at δ=2.27 ppm from compound of formula (VI))/6.

$^1$H-NMR Measurements of the Inventive Solution:

Prior to $^1$H-NMR measurements, the inventive solution is reacted with excess phenyl hydrazine (approx. 2 mol per mol of compound of formula (I) plus (III) to convert the N-oxyl radicals to the corresponding hydroxylamines. This procedure yields two isomeric forms of each reduced species (compound of formula (Ia) and (Ib)/compound of formula (IIa) and (IIIb)) and each isomer gives individual signals in the $^1$H-NMR spectrum. For all $^1$H-NMR measurements the crude reaction mixture from reduction with phenyl hydrazine was diluted with $D_2O$ and referenced to the signal of residual $H_2O$ protons at δ=4.79 ppm.

Signal assignments for compound of formula (I) were confirmed by synthesizing compound of formula (I) as a pure crystalline material as described in WO 2018/2883011 on page 28. Signal assignments for compound of formula (III) were confirmed by synthesizing compound of formula (III) as a pure material in aqueous solution as described here.

Synthesis of Compound of Formula (III) in Pure Form in Aqueous Solution:

To a solution of compound of formula (IV) (39.3 g) in water (40.1 g), 37 wt.-% hydrochloric acid (11.97 g) is added, whereby the pH value of the solution decreases to 9.0. Then, solid sodium bicarbonate (2.71 g) is added and the mixture is heated to 60° C. When this temperature is reached a 50 wt.-% aqueous solution of hydrogen peroxide (46.4 g) is continuously added over a period of 4 hours. During addition the pH value decreases and is kept above 8.0 by the addition of a 50 wt.-% aqueous solution of sodium hydroxide (6.4 g) in five approximately equal portions. After the addition of the hydrogen peroxide is completed, stirring is continued for 12 hours. Then, the mixture is allowed to cool down to room temperature and analyzed by 1H NMR spectroscopy and ESI MS mass spectrometry. The mixture contains >99 wt.-% of compound of formula (III) as organic material as determined by 1H NMR.

The identity of compound of formula (I) and (III) is also supported by HRMS (ESI in ACN:$H_2O$:HCOOH=80:20:0.1, instrument: Q Extractive™ hybrid-quadrupole-orbitrap mass spectrometer, ThermoFisher).

$^1$H-NMR of the Reduced Form of Compound of Formula (I):

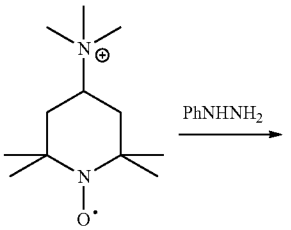

(I)

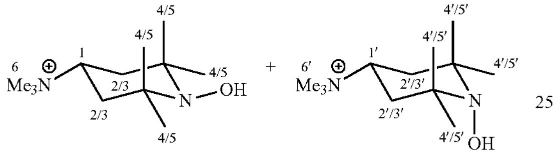

(Ia and Ib)

$^1$H-NMR (500 MHz, $D_2O$): δ [ppm]=3.80-3.67 (m, 1H, $H_1$+$H_{1'}$), 3.12 (s, 9H, $H_6$ or $H_6$, minor isomer), 3.09 (s, 9H, $H_6$ or $H_{6'}$, major isomer), 2.24-2.14 (m, 2H, $H_2$+$H_{2'}$), 1.99 (t, J=12.1 Hz, 2H, $H_3$ or $H_{3'}$, minor isomer), 1.75 (t, J=12.4 Hz, 2H, $H_3$ or $H_{3'}$, major isomer), 1.34 (s, 6H, $H_{4/5}$ or $H_{4/5'}$, minor isomer), 1.26 (s, 6H, $H_{4/5}$ or $H_{4/5'}$, major isomer), 1.22 (s, 6H, $H_{4/5}$ or $H_{4/5'}$, major isomer), 1.12 (s, 6H, $H_{4/5}$ or $H_{4/5'}$, minor isomer). The ratio of the two isomers is approximately 90:10.

HRMS: theory for $C_{12}H_{26}N_2O^+$: 214.2040; found: 214.2036.

$^1$H-NMR of the Reduced Form of Compound of Formula (III):

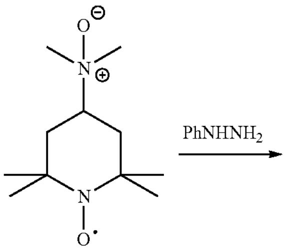

(III)

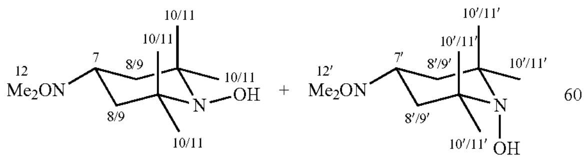

(IIIa and IIIb)

$^1$H-NMR (500 MHz, $D_2O$): δ [ppm]=3.66-3.52 (m, 1H, $H_7$+$H_{7'}$), 3.17 (s, 6H, $H_{12}$ or $H_{12'}$, minor isomer), 3.14 (s, 6H, $H_{12}$ or $H_{12'}$, major isomer), 2.27-2.14 (m, 2H, $H_8$+$H_{8'}$), 1.93 (t, J=12.5 Hz, 2H, $H_9$ or $H_{9'}$, minor isomer), 1.72 (t, J=12.5 Hz, 2H, $H_9$ or $H_{9'}$, major isomer), 1.33 (s, 6H, $H_{10/11}$ or $H_{10'/11'}$, minor isomer), 1.25 (s, 6H, $H_{10/11}$ or $H_{10'/11'}$, major isomer), 1.21 (s, 6H, $H_{10/11}$ Or $H_{10/11'}$, major isomer), 1.11 (s, 6H, $H_{10/11}$ or $H_{10/11'}$, minor isomer). The ratio of the two isomers is approximately 86:14.

HRMS: theory for $C_{11}H_{24}N_2O_2^+$: 216.1638; found: 216.1637.

Compound of formula (II) remains unchanged in the reduction and gives signals that are well separated from the signals from compound of formula (Ia), (Ib), (IIIa) and (IIIb):

(II)

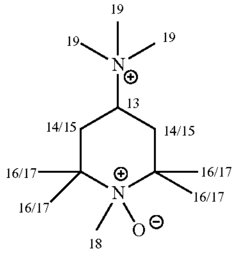

$^1$H-NMR (500 MHz, $D_2O$): δ [ppm]=3.93 (tt, J=13.3 Hz, 3.2 Hz, 1H, $H_{13}$), 3.14 (s, 9H, $H_{19}$), 3.03 (s, 3H, $H_{18}$), 2.47 (t, J=12.6 Hz, 2H, $H_{14}$), 2.07 (d, J=12.1 Hz, 2H, $H_{15}$, 1.65 (s, 6H, $H_{16}$), 1.56 (s, 6H, $H_{17}$).

HRMS: theory for $C_{13}H_{29}N_2O^+$: 229.2274; found: 229.2271.

The ratio of compound of formula (I), (II) and (III) can be determined most conveniently by comparing the integrals of the $^1$H-NMR signals at δ=3.80-3.67 ppm (1H from compound of formula (I)), 1.56 ppm (6H from compound of formula (II)) and 3.66-3.52 ppm (1H from compound of formula (III)).

Thus the molar ratio of compound of formula (I):(II):(III) is the same as the ratio of the following integrals:

(integral of signal at δ=3.80-3.67 ppm from compound of formula (I)):(integral of signal at δ=1.56 ppm from compound of formula (II))/6:(integral of signal at δ=3.66-3.52 ppm from compound of formula (III)

Cerimetric Redox Titration:

Cerimetric redox titration is used to determine the total content of hydrogen peroxide and N-oxyl species (compound of formula (I)+(III)) according to the following method:

Content of N-Oxyl Species:

100 mg of manganese dioxide is added to approx. 1 g of analyte. The mixture is stirred at 20 to 25° C. for 5 minutes or until 5 minutes after the end of gas evolution. Then the analyte is filtered. 250±2 mg of filtered analyte is placed in a beaker equipped with a magnetic stirring bar and is diluted with 45 mL purified water and 5 mL dilute sulfuric acid (10 wt.-% in water). The obtained solution is placed on an automated titration device (905 Titrando, Metrohm) equipped with a Pt-Titrode (Metrohm) and is stirred at 20-25° C. Cerium (IV) sulfate solution (0.10 mol/L) is added via the titration device until a redox potential jump is detected ($V_{C1}$). The concentration of the sum of compound of formula (I)+(III) in weight-%, $w_{I+III}$, can then be calculated from the consumption of cerium (IV) sulfate solution using the following equation:

$$w_{I+III} = 100 * \frac{V_{c1} * C_c}{m_s} * [(x_I * M_{I-Cl}) + (x_{III} * M_{III})]$$

Where the symbols have the following meaning:

$V_c$ is the volume of the cerium sulfate solution used given in liter $C_{c1}$ is the concentration of the cerium sulfate solution used given in mol/liter $m_s$ is the mass of the analyte given in grams $M_{I-Cl}$ is 249.8 g/mol, the molar mass of compound of formula (I) as the chloride salt $M_{III}$ is 215.3 g/mol, the molar mass of compound of formula (III)

$x_I$ is the molar fraction of compound of formula (I) calculated as the ratio of (integral at δ=3.80-3.67 ppm in $^1$H-NMR):[(integral of signal at δ=3.66-3.52 ppm in $^1$H-NMR)+(integral at δ=3.80-3.67 ppm in $^1$H-NMR)]

$x_{III}$ is the molar fraction of compound of formula (III) calculated as the ratio of (integral of signal at δ=3.66-3.52 ppm in $^1$H-NMR):[(integral of signal at δ=3.66-3.52 ppm in $^1$H-NMR)+(integral at δ=3.80-3.67 ppm in $^1$H-NMR)]

Sum of Hydrogen Peroxide and N-Oxyl Species:

250±2 mg of analyte is placed in a beaker equipped with a magnetic stirring bar and is diluted with 45 mL purified water and 5 mL dilute sulfuric acid (10 wt.-% in water). The obtained solution is placed on an automated titration device (905 Titrando, Metrohm) equipped with a Pt-Titrode (Metrohm) and is stirred at 20-25° C. Cerium (IV) sulfate solution (0.10 mol/L) is added via the titration device until a redox potential jump ($V_{C2}$) is detected. The concentration of hydrogen peroxide can be calculated from the difference of the consumptions of cerium (IV) sulfate solution ($\Delta V_C = V_{C2} - V_{C1}$) using the following equation:

$$w_{H_2O_2} = 100 * \frac{\Delta V_c * C_c}{m_s} * M(H_2O_2)$$

Where the symbols have the same meanings as defined above and $M_{H2O2}$ is 34.0 g/mol, the molar mass of hydrogen peroxide.

Cyclic Voltammetry Method:

The solution obtained from the respective example is diluted with 0.1 mol/L aqueous sodium chloride solution until the concentration of the N-oxyl compounds is 1.0 wt.-%. Said solution is placed in an electrochemical cell equipped with a standard 3 electrode setup (working electrode: glassy carbon (ø=2 mm), counter electrode: platinum wire, reference electrode: Ag/AgCl, 3 mol/L KCl in water). The potential is ramped to 1200 mV and then cycled between 1200 mV and −700 mV at a scan rate of ±20 mV/s (in total 3 cycles) using PGU 20V-2A-E potentiostat (IPS).

Example 1

In a stainless-steel autoclave 92 g (116.5 ml) of methanol, 40.0 g of compound of formula (IV) and 23.5 g dimethyl carbonate are mixed and heated to 120° C. The mixture is stirred for 24 h at 120° C. Then the autoclave is allowed to cool down to room temperature and depressurized. Volatiles are distilled off and a solid residue (49.6 g) is obtained and dissolved in 50 g water to obtain a 50 wt.-% aqueous solution of compound of formula (IV), (V) and (VI) as a clear yellowish solution. The ratio of compound of formula (IV):(V):(VI) as determined by 1H-NMR is 1.0: 98.1:0.9, which corresponds to 0.4 wt.-% of compound of formula (IV), 49.1 wt.-% of compound of formula (V) carbonate salt and 0.5 wt.-% of compound of formula (VI) carbonate salt.

Example 2

In a stainless-steel autoclave 92 g (116.5 ml) of methanol, 40.0 g of compound of formula (IV) and 23.5 g dimethyl carbonate are mixed and heated to 120° C. The mixture is stirred for 24 h at 120° C. Then the autoclave is allowed to cool down to room temperature and depressurized. Then, 40 mL of water are added, the mixture is heated to 90° C. and 46.1 g distillate are collected. Another 40 g of water are added to the sump, the mixture is heated to 107° C. and 47.9 g of distillate are collected. The sump (124.6 g) is a 40 wt.-% solution of compound of formula (IV), (V) and (VI) in water. The ratio of compound of formula (IV):(V):(VI) as determined by 1H-NMR is 1.0:98.1:0.9, which corresponds to 0.3 wt.-% of compound of formula (IV), 39.3 wt.-% of compound of formula (V) carbonate salt and 0.4 wt.-% of compound of formula (VI) carbonate salt. No methanol is found in the NMR.

Example 3 (Comparative)

The methylation was made as described in the WO 2018/28830, page 27, line 20 to page 28 line 15 (entspricht DE102016009904A1, paragraph and following). In the $^1$H-NMR of the product obtained, only signals for compound of formula (V) are visible.

Example 4

To a solution taken from example 1 (100 g, contains 0.4 wt.-% compound of formula (IV), 49.1 wt.-% of compound of formula (V) carbonate salt and 0.5 wt.-% of compound of formula (VI) carbonate salt in water) 37 wt.-% hydrochloric acid (0.82 g) is added, whereby the pH value of the solution decreases to 10.0. Then the mixture is heated to 60° C. When the temperature is reached a 50 wt.-% aqueous solution of hydrogen peroxide (32.7 g) is continuously added over a period of 4 hours. After the addition of the hydrogen peroxide is completed, stirring is continued for 12 hours. The mixture is then allowed to cool down to about 30° C. and 37 wt.-% hydrochloric acid (ca. 19 g) is added to decrease the pH value of the solution to 4.3. Water is consequently distilled off at reduced pressure (70 mbar abs) until the concentration of N-oxyl species of compound of formula (I) and (III) is 50 wt.-% (as determined by cerimetric redox titration). The molar ratio of compound of formula (I):(II):(III) as determined by 1H-NMR is 98.1:0.8:1.1 which corresponds to 49.5 wt.-% of compound of formula (I) chloride salt, 0.4 wt.-% of compound of formula (II) chloride salt and 0.5 wt.-% of compound of formula (III).

Example 5

To a solution taken from example 1 (100 g, contains 0.4 wt.-% of compound of formula (IV), 49.1 wt.-% of compound of formula (V) carbonate salt and 0.5 wt.-% of compound of formula (VI). carbonate salt in water) 10 wt.-% nitric acid (21.1 g) is added, whereby the pH value of the solution decreases to 9.5. Then the mixture is heated to 60° C. When the temperature is reached a 50 wt.-% aqueous solution of hydrogen peroxide (32.7 g) is continuously added over a period of 2 hours. After the addition of the hydrogen peroxide is completed, stirring is continued for 12 hours. The mixture is then allowed to cool down to about 30° C. and 10 wt.-% nitric acid (ca. 19 g) is added to decrease the pH value of the solution to 4.5. Water is consequently distilled off at reduced pressure (70 mbar abs) until the concentration of N-oxyl species of compound of formula (I) and (III) is 49 wt.-% (as determined by cerimetric redox titration).

The molar ratio o compound of formula (I):(II):(III) as determined by 1H-NMR is 98.1:0.8:1.1, which corresponds to 48.6 wt.-% of compound of formula (I) nitrate salt, 0.4 wt.-% of compound of formula (II) nitrate salt and 0.5 wt.-% of compound of formula (III).

Example 6 (Comparative)

The oxidation was performed as described in the WO 2018/028830, page 28, line 20 to page 29 line 22. In HRMS of the product obtained no signals for compound of formula (II) and (IIIa)/(IIIb) are visible; in $^{1}$H-NMR of the reduced samples only signals for compound of formula (Ia/Ib) are visible.

BRIEF DESCRIPTION OF THE FIGURES

Example 7

Cyclic voltammogram of the product from example 4 (see Figure I).

Example 8

Figure 1:
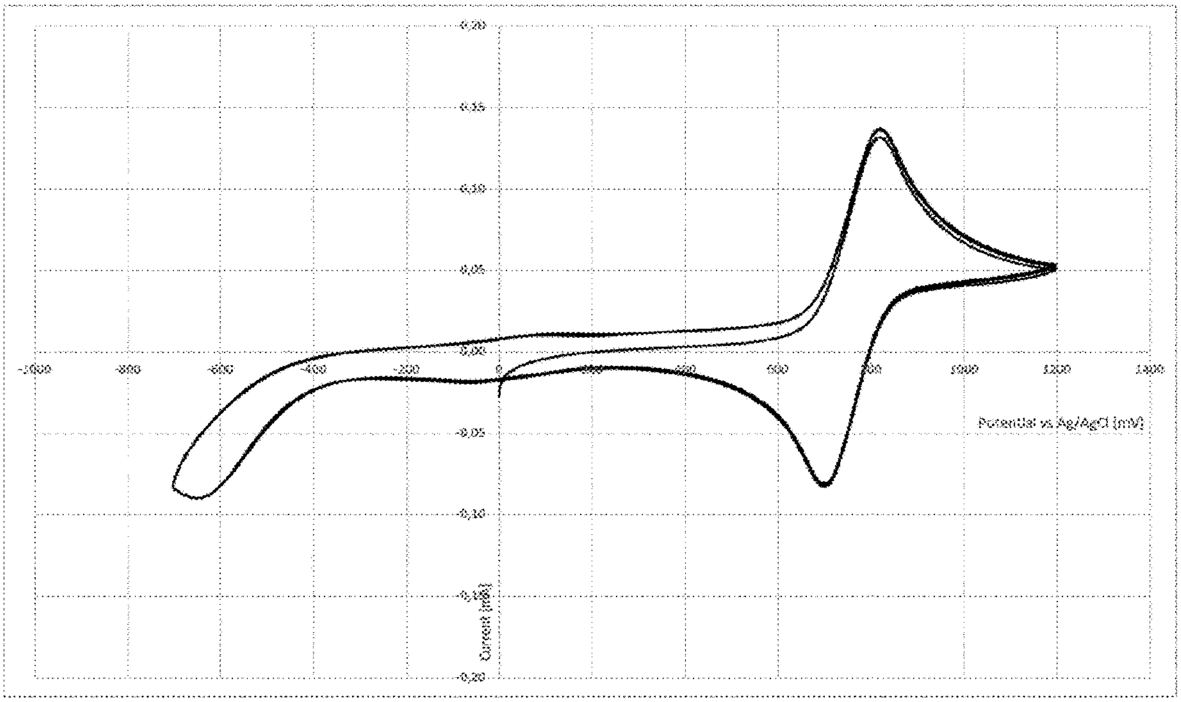
Figure 2:
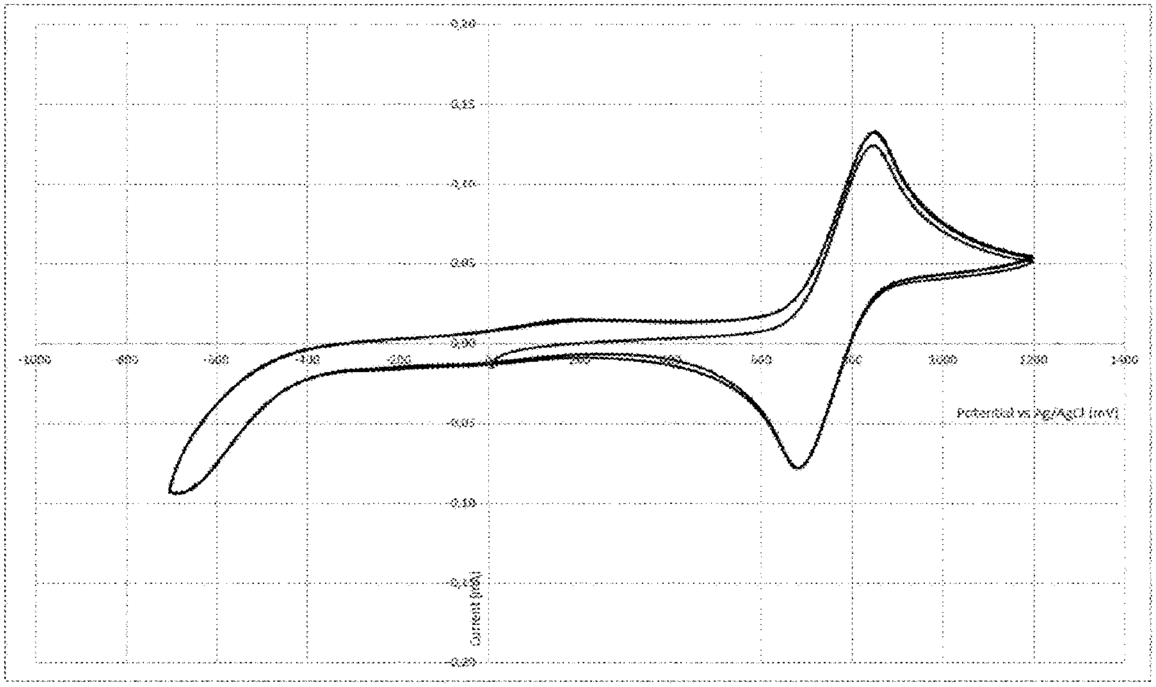
Figure 3:
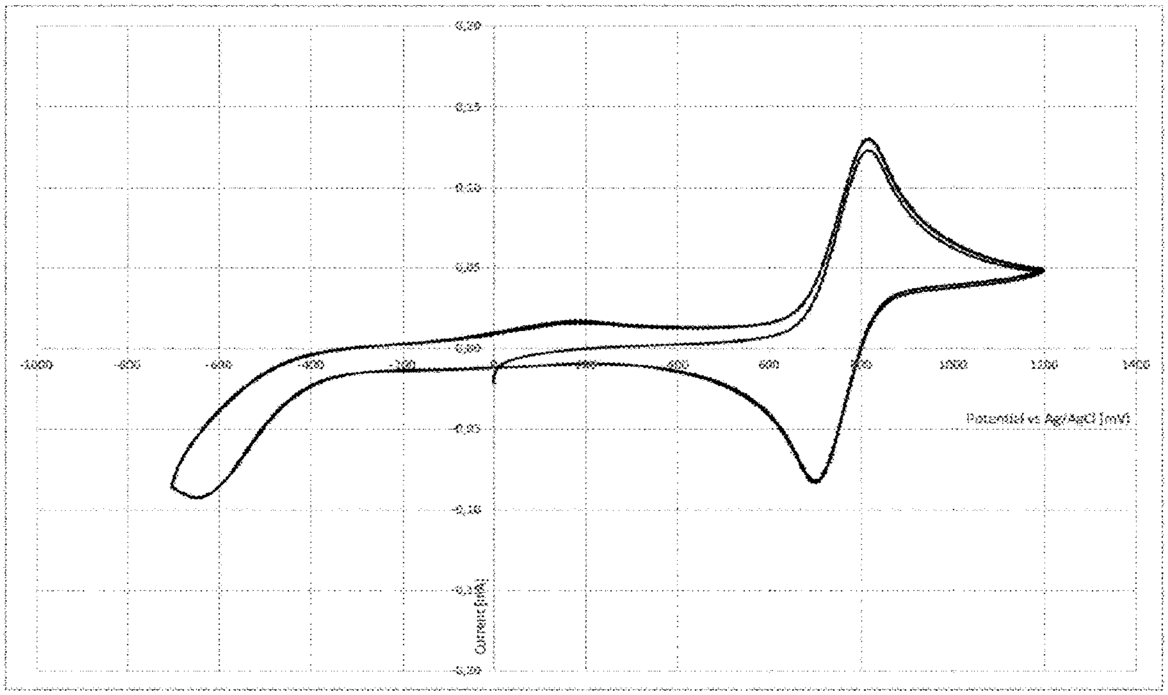

Cyclic voltammogram of the product from example 5 (see Figure II).

Example 9

Cyclic voltammogram of the product from example 6 (see Figure III).

The cyclic voltammogram in Figure I and II are nearly identical to that of the comparative example 6 in Figure III. Therefore, the inventive solution of example 4 and 5 show nearly the same redox potential as the solution obtained in example 5 which represents the state of the art. The inventive solution can thus be used in a redox flow cell as it is described in the state of the art.

The invention claimed is:

1. A solution comprising a) water, b) 20 to 55 wt.-% according to the total weight amount of the solution of compound 2,2,6,6-tetramethyl-4-(trimethylammonio)-1-piperidinyloxy of formula (I), (I)

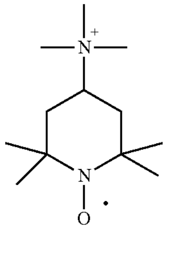

c) less than 0.1 wt.-% according to the total weight amount of the solution alkali metal cation d) 0.1 to 12.5 wt.-% according to the total weight amount of the solution of compound N,N,N,1,2,2,6,6-octamethyl-4-piperidinammonium-1-oxide of formula (II)

(II)

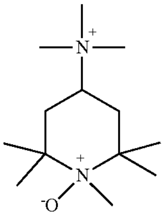

e) 0.01 to 20 wt.-% according to the total weight amount of the solution of compound 2,2,6,6-hexamethyl-4-(dimethylamino)-1-piperidinyloxy-N-oxide of formula (III)

(III)

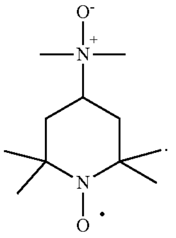

2. The solution according to claim 1 wherein the alkali metal cation is Na.

3. The solution according to claim 1 wherein the solution has a pH-value in the range of 2 to 7.

4. The solution according to claim 1 wherein the sum of the amounts of the compounds of formula (I), (II), (III) plus the amounts of alkali metal cations in the solution is in the range of 20 to 50 wt.-% with respect to the total weight amount of the solution.

5. A process for the production of the solution according to claim 1 comprising the following steps:

i) reacting the compound N,N,2,2,6,6-hexamethyl-4-piperidinamine of formula (IV)

(IV)

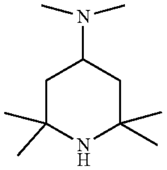

with dimethyl carbonate in the presence of a saturated C1 to C4-alcohol to get a mixture comprising compound N,N,N,2,2,6,6-heptamethyl-4-piperidinaminium of formula (V), compound N,N,N,1,2,2,6,6-octamethyl-4-piperidinaminium of formula (VI) and non-reacted compound N,N,2,2,6,6-hexamethyl-4-piperidinamine of formula (IV) dissolved in the saturated C1 to C4 alcohol (IV)

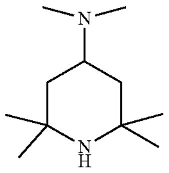

(V)

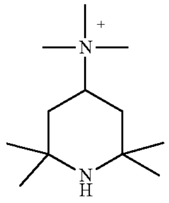

(VI)

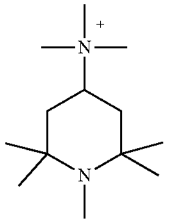

ii) making a solvent change from the C1 to C4 alcohol to water iii) reacting the resulting aqueous mixture of step ii) with an aqueous hydrogen peroxide solution, iv) adding an acid to the resulting mixture of step iii) until the pH-value decreases to the range of 3 to 5, v) partially removing the water of the resulting mixture of step iv) until the concentration of compound of formula (I) is in the range of 20 to 55 wt.-% according to the solution of claim 1.

6. The process of claim 5 wherein in step i) of the process the compound of formula (IV) is reacted with dimethyl carbonate in the presence of a saturated C1 to C4 alcohol at a temperature in the range of 90 to 170° C.

7. The process according to claim 5 wherein in step i) of the process the compound of formula (IV) is reacted with 0.7 to 1.5 mol dimethyl carbonate in the present of a saturated C1 to C4 alcohol and the mass ratio between compound of formula (IV) in the feed mixture and the saturated C1 to C4 alcohol is in the range of 0.1 to 5.

8. The process according to claim 5 wherein in step iii) of the process the resulting mixture of step ii) is reacted with an aqueous hydrogen peroxide solution at a temperature in the range of 20 to 80° C.

9. The process according to claim 5 wherein in step iii) of the process 1.5 to 5 mol of aqueous hydrogen peroxide having a concentration in the range of 25 to 70 wt.-% are used per mol of compound of formula (IV) in the feed mixture.

10. The process according to claim 5 wherein the addition of the acid in step iv) will start when the concentration of hydrogen peroxide in the mixture of step iii) has decreased to less than 0.5 wt.-%.

11. The process according to claim 5 wherein the acid used in step iv) has a standard redox potential greater than +1.35 V.

12. The process according to claim 5 wherein in step ii) of the process the C1 to C4 alcohol is first distilled off and the remaining material is dissolved in water.

13. The process according to claim 5 wherein in step ii) of the process water is added to the resulting mixture of step i) and afterwards or simultaneously the C1 to C4 alcohol is distilled off.

14. The process according to claim 13 wherein the saturated C1 to C4 alcohol is selected from the group of methanol and n-butanol.

15. A process for making a redox-flow cell wherein a solution according to claim 1 is used as electrolyte in one of both chambers of the cell.

16. The process according to claim 15 comprising the following steps:

a) providing two chambers for catholyte and anolyte solutions, each connected to at least one storage tank for catholyte and anolyte solutions respectively b) separating the two chambers with an ion-conducting membrane c) equipping the chambers with electrodes d) filling the solution comprising a 2,2,6,6-tetramethyl-4-(trimethylammonio)-1-piperidinyloxy salt as redox active material in the catholyte chamber e) filling an anolyte solution comprising another redox active material in the anolyte chamber.

17. A redox-flow cell obtained by a process according to claim 15.

18. A method of using the redox flow cell according to claim 17 for storing electrical energy.

* * * * *